US011065275B2

(12) United States Patent
Ambati et al.

(10) Patent No.: US 11,065,275 B2
(45) Date of Patent: Jul. 20, 2021

(54) CROSS-LINKING AGENTS AND ASSOCIATED METHODS (71) Applicant: University of Utah Research Foundation, Salt Lake City, UT (US)

(72) Inventors: Balamurali K. Ambati, Sandy, UT (US); Hironori Uehara, Salt Lake City, UT (US); Santosh Muddana, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/083,865

(22) PCT Filed: Dec. 6, 2016

(86) PCT No.: PCT/US2016/065215
§ 371 (c)(1),
(2) Date: Sep. 10, 2018

(87) PCT Pub. No.: WO2017/155580
PCT Pub. Date: Sep. 14, 2017

(65) Prior Publication Data
US 2019/0083529 A1    Mar. 21, 2019

Related U.S. Application Data (60) Provisional application No. 62/305,227, filed on Mar. 8, 2016.

(51) Int. Cl.
*A61K 33/34* (2006.01)
*A61K 9/00* (2006.01)
*A61P 27/02* (2006.01)
*A61K 9/06* (2006.01)
*A61K 9/08* (2006.01)
*A61K 31/198* (2006.01)
*A61K 31/525* (2006.01)
*A61K 31/352* (2006.01)
*A61K 45/06* (2006.01)

(52) U.S. Cl.
CPC ............ *A61K 33/34* (2013.01); *A61K 9/0048* (2013.01); *A61K 9/0051* (2013.01); *A61K 9/06* (2013.01); *A61K 9/08* (2013.01); *A61K 31/198* (2013.01); *A61K 31/525* (2013.01); *A61P 27/02* (2018.01); *A61K 31/352* (2013.01)

(58) Field of Classification Search
CPC .. A61K 2300/00; A61K 31/352; A61K 33/34; A61K 31/198; A61K 31/525; A61K 9/0048; A61K 9/0051; A61K 9/06; A61K 9/08; A61K 45/06; A61P 27/02
See application file for complete search history.

(56) References Cited

U.S. PATENT DOCUMENTS

| 4,490,389 | A | 12/1984 | Nelson et al. |
| 7,351,715 | B2 * | 4/2008 | Richardson .......... A61K 9/0034 424/464 |
| 2003/0175259 | A1 | 9/2003 | Karageozin et al. |
| 2006/0029636 | A1 | 2/2006 | Hendriks |
| 2006/0134226 | A1 * | 6/2006 | Leonard ............... A61K 31/047 424/638 |
| 2006/0165611 | A1 | 7/2006 | Maurer |
| 2006/0276777 | A1 | 12/2006 | Coroneo |
| 2010/0016814 | A1 | 1/2010 | Gokhale et al. |
| 2010/0189817 | A1 | 7/2010 | Krueger et al. |
| 2011/0076285 | A1 | 3/2011 | Stalmans et al. |
| 2016/0059032 | A1 | 3/2016 | Skerl |

FOREIGN PATENT DOCUMENTS

RU   WO 2014/204357 A2 * 12/2014 ............. A61K 31/13
WO   WO 2014/065863           5/2014

OTHER PUBLICATIONS

German et al.; Eye (1999) 13, pp. 93-100.*
Young, Matt; EyeWorld "Crosslinking for Keratitis"; Feb. 2010 (www.eyeworld.org/article-crosslinking-for-keratitis); attached as 7-pg pdf.*
Machine translation of WO 2014/204357 A2; provided via Espacenet on Nov. 11, 2020; published Dec. 24, 2014.*
"Medical Calculations"; (www.vettechprep.com/_pps/ EWHTIGRJJTDUZGU29006.pdf); published byVetTechPrep.com; copyright 2018.*
Wollensak et al.; "Riboflavin /Ultraviolet-A-induced collagen crosslinking for the treatment of keratoconus". Am J Ophthalmol. 2003, 135, 620-62. InternetAdvance publication at ajo.com Feb. 26, 2002.*
IQQueryQuickExport202102060147—NPLsearch results; downloaded Feb. 5, 2021.*
Dudakova, L. et al; "Is copper imbalance an environmental factor influencing keratoconus development?" Medical Hypotheses, vol. 84, Issue 5, 2015, pp. 518-524, ISSN 0306-9877, https://doi.org/10.1016/j.mehy.2015.02.017. (https://www.sciencedirect.com/science/article/pii/S0306987715000948).
Avetisov SE, et al.; "The role of tear acidity and Cu-cofactor of lysyl oxidase activity in the pathogenesis of keratoconus"; Vestn Oftalmol. Mar.-Apr. 2011;127(2):3-8. Russian. PMID: 21721263.
Dudakova, L. et al.; "Changes in lysyl oxidase (LOX) distribution and its decreased activity in keratoconus corneas" Exp Eye Res. Nov. 2012;104:74-81. doi: 10.1016/j.exer.2012.09.005. Epub Oct. 3, 2012. PMID: 23041260.

* cited by examiner

Primary Examiner — Jeffrey T. Palenik
(74) Attorney, Agent, or Firm — Thorpe North and Western, LLP; David W. Osborne (57) ABSTRACT An ophthalmic composition or dosage form can include a therapeutically effective amount of a cross-linking agent and a pharmaceutically acceptable carrier. The composition or dosage form can be used to treat an ophthalmic condition by administering a therapeutically effective amount of the composition to an eye of a subject during a treatment period.

13 Claims, 9 Drawing Sheets

Human Normal Cornea:

FIG. 2C

Human Keratoconus Cornea (Cu Treated)

FIG. 3A

*Human Keratoconus Cornea (No Cu Treated)*

FIG. 3B

*Human Normal Cornea:*

CROSS-LINKING AGENTS AND ASSOCIATED METHODS

RELATED APPLICATIONS

This application claims the benefit of U.S. Provisional Application Ser. No. 62/305,227, filed on Mar. 8, 2016, which is incorporated herein by reference.

BACKGROUND

A number of ophthalmic conditions can result in corneal thinning and biomechanical weakness of the cornea. In some cases, the shape of the cornea can be altered, causing distorted vision, sensitivity to light, and other complications. Such conditions can include keratoconus, corneal ulcers, corneal ectasia, pellucid marginal degeneration, and the like.

For example, keratoconus (KCN) is a progressive disorder associated with structural changes in corneal collagen organization that can lead to corneal thinning and ruptures in Bowman's layer and/or Descemet's membrane. Typically, the disease manifests in the second decade of life when the cornea assumes a more conical shape, which leads to irregular astigmatism, progressive myopia, corneal thinning and subsequently poor visual acuity. The prevalence of KCN is variable and depends on genetic, geographic, ethnic, gender, and diagnostic considerations with the most cited prevalence at 50 per 100,000. The severity of KCN is often assessed by minimum corneal thickness, inferior-superior or inter-eye asymmetry, maximum keratometry, or corneal hysteresis.

BRIEF DESCRIPTION OF THE DRAWINGS

These drawings are provided to illustrate various aspects of the invention and are not intended to be limiting of the scope in terms of dimensions, materials, configurations, arrangements or proportions unless otherwise limited by the claims.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a cell" includes a plurality of such cells.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in the written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The term "coupled," as used herein, is defined as directly or indirectly connected in a chemical, mechanical, electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the terms "therapeutic agent," "active agent," and the like can be used interchangeably and refer to agent that can have a beneficial or positive effect on a subject when administered to the subject in an appropriate or effective amount. In one aspect, the therapeutic or active agent can be a copper-containing compound.

As used herein, an "effective amount" of an agent is an amount sufficient to accomplish a specified task or function desired of the agent. A "therapeutically effective amount" of a composition, drug, or agent refers to a non-toxic, but sufficient amount of the composition, drug, or agent, to achieve therapeutic results in treating or preventing a condition for which the composition, drug, or agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician, veterinarian, or other qualified medical personnel using evaluations known in the art, it is recognized that individual variation and response to treatments may make the achievement of therapeutic effects a somewhat subjective decision. The determination of an effective amount or therapeutically effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986).

As used herein, a "dosing regimen" or "regimen" such as "treatment dosing regimen," or a "prophylactic dosing regimen" refers to how, when, how much, and for how long a dose of an active agent or composition can or should be administered to a subject in order to achieve an intended treatment or effect.

As used herein, the terms "treat," "treatment," or "treating" refers to administration of a therapeutic agent to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid, liquid (i.e. solution), or gas. Furthermore, the term "dosage form" can include one or more formulation(s) or composition(s) provided in a format for administration to a subject. For example, an injectable dosage form would be a formulation or composition prepared in a manner that is suitable for administration via injection.

As used herein, a "subject" refers to an animal. In one aspect the animal may be a mammal. In another aspect, the mammal may be a human.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

In one example, an ophthalmic composition or dosage form is described herein. The ophthalmic composition or dosage form can include an amount of a cross-linking agent, such as a copper-containing agent, that is sufficient to increase lysyl oxidase activity in an eye of a subject or otherwise increase cross-linking in the cornea of the subject. The composition or dosage form can further include a pharmaceutically acceptable carrier. In some examples, the dosage form can be an ophthalmic composition formulated as a topical eye drop and carried in a container adapted to dispense the composition in a drop-wise manner at a drop volume of from about 5 µl to about 50 µl. In another embodiment, a method is described for using such a composition or dosage form. The method can include administering a therapeutically effective amount of a composition or dosage form, as described herein, during a treatment period.

As will be more apparent by the various embodiments and examples provided herein, the compositions, dosage forms, and methods described in the current disclosure can increase corneal lysl oxidase activity in an eye of a subject, can increase corneal tissue strength in an eye of a subject, and can provide a number of other benefits described herein.

With this in mind, the compositions, dosage forms, and methods can be used to treat a variety of ophthalmic indications. For example, a variety of ophthalmic conditions can cause corneal thinning, biomechanical weakness of the cornea, and other corneal complications. Such conditions can include corneal ulcers, peripheral ulcerative keratitis, corneal melts, pellucid marginal degeneration, Terrien's marginal degeneration, neurotrophic disease of the cornea, corneal ectasia (such as after refractive surgery), keratoconus, the like, or combinations thereof. The current disclosure describes compositions, dosage forms, and methods for treating these conditions, similar conditions, or combinations thereof. However, for the sake of brevity, specific mention will be made to the example condition of keratoconus throughout. This focus on keratoconus is merely for illustrative purposes and is not intended to be limiting in any way.

With that in mind, keratoconus (KCN) is a corneal disease characterized by non-inflammatory, gradual thinning and ectasia of the stroma, scarring, and eventual ruptures of Descemet's membrane. The prevalence of KCN is variable and depends on genetic, geographic, ethnic, gender, and diagnostic considerations with the most cited prevalence at 50 per 100,000. The severity of KCN is dependent on corneal biomechanical strength, often assessed by thinnest corneal thickness. However, this criterion is being replaced by emerging parameters such as posterior corneal elevation, corneal hysteresis, and cross-links of collagen per unit corneal thickness. The last measurement takes into account the ethnic and gender differences in corneal collagen content inherent in the population.

The consequences of KCN are as variable as its epidemiology, ranging from mild astigmatism to severely distorted vision. However, treatment options are surprisingly limited. Most mild KCN can be corrected with glasses or soft contacts but very often patients will need toric or hard contacts as the disease progresses. Ultimately, 1 in 5 patients will require surgery, most commonly deep anterior lamellar keratoplasty or a penetrating corneal transplant. Such procedures require considerable costs and entail significant risk of intraoperative and post-operative complications (bleeding, scarring, cataract formation, etc.). Thus, more effective pre-surgical treatment options are desperately needed.

Intacs (clear crescent-shaped pieces of plastic polymer) have been used as a treatment option for mild to moderate keratoconus. These intrastomal corneal rings are inserted as a minimally invasive procedure and have a 74% success rate at restoring 20/20 best-corrected vision. However, cost and risk (neovascularization, channel deposits, secondary surgery etc.) are again limiting.

Methods to strengthen collagen cross-links have also been attempted. Corneal Collagen Cross-link (CXL) therapy is a well-tolerated technique where riboflavin drops are applied over or under the corneal epithelium and ultraviolet-A light is then employed to release free oxygen radicals to strengthen collagen bonds. This procedure has been shown to significantly delay or halt progression of KCN. Although this technique carries minimal side-effects (the energy-rich UVA light and excessively high concentration of free oxygen radicals can cause toxicity), it is still cost-prohibitive to many subjects.

The current disclosure describes an alternative composition, dosage form, and method for strengthening collagen cross-links using a cross-linking agent, such as a copper-containing agent, a calcium-containing agent, a magnesium-containing agent, a silver-containing agent, an aluminum-containing agent, a zinc-containing agent, iron-containing agent, or other suitable cross-linking agent. Some specific, but non-limiting, examples of cross-linking agents can include acai extract, decorin, copper (II) sulfate, or combinations thereof. In some examples, the cross-linking agent can be or include any divalent or multivalent ion or compound that is suitable to induce or facilitate cross-linking in the cornea. In some examples, the cross-linking agent can be or include a metal ion, such as an alkaline earth metal, a transition metal, a post-transition metal, or combinations thereof, for example. In some examples, the cross-linking agent can be or include a cation. In some specific examples, the cross-linking agent can be or include a divalent metal ion, such as copper, magnesium, iron, zinc, or the like. However, for the sake of brevity and clarity, specific reference will be made throughout the present disclosure to copper-containing agents as an example of a suitable cross-linking agent. This focus on copper-containing agents is merely for illustrative purposes and is not intended to be limiting in any way.

Copper is a co-factor for lysyl oxidase (LOX), an enzyme that forms various types of collagen cross-links. A single nucleotide polymorphism of LOX, rs1800449, increases the genetic risk for KCN. Further, patient KCN tissues exhibit lower LOX activity. Thus, copper deficiency can cause reductions in collagen content in tissues. As such, copper supplementation via a copper-containing salt, compound, chelate, or the like can be used to increase collagen bonds. Such supplementation can improve the biomechanical properties of diseased corneas by increasing lysyl oxidase activity. Because low LOX activity in the cornea can contribute to the development of KCN and copper supplementation can improve collagen cross-links, topical copper treatment can provide a non-evasive and relatively cost effective tool for preventing the progression of KCN.

Accordingly, an ophthalmic composition or dosage form is described herein that can include an amount of a cross-linking agent, such as a copper-containing agent, that is sufficient to increase lysyl oxidase activity in an eye of a subject or otherwise increase corneal cross-linking. A variety of copper-containing agents can be used, such as a copper-containing salt, compound, chelate, or the like. Non-limiting examples of copper salts can include copper sulfates, copper carbonates, copper acetates, copper chlorides, copper bromides, copper fluorides, copper nitrates, copper iodides, copper perchlorates, copper molybdates, copper thiocyanates, copper tartrates, copper tetrafluoroborates, copper selenides, copper pyrophosphates, the like, or combination thereof. Other suitable copper carriers can include GHK-copper, tetra-amine copper sulfate, copper-histidine, copper-glycinate, copper-gluconate, the like, or combinations thereof.

Thus, the copper-containing agent can be any suitable copper-containing agent that can provide a therapeutically effective amount of bioavailable copper. The therapeutically effective amount can be sufficient to increase corneal lysyl oxidase activity in the eye such that collagen cross-linking is increased as compared to collagen cross-linking prior to treatment. This can also increase the biomechanical strength of the cornea as compared to the biomechanical strength prior to treatment. Further, this can decrease the diopter of the cornea in the treated eye as compared to the diopter prior to treatment.

A therapeutically effective amount of a copper-containing agent can be based upon the amount of copper carried by the copper-containing agent. In some examples, the copper-containing agent can provide copper levels less than about 0.05 mg/ml, about 0.02 mg/ml, about 0.005 mg/ml, or about 0.002 mg/ml, but that are still effective at increasing lysyl oxidase activity. It can be important to keep the copper level sufficiently low to avoid copper-induced toxicity, while maintaining a sufficient amount of bioavailable copper to increase lysyl oxidase activity.

Thus, the therapeutically effective amount of the copper-containing agent can be determined based on the type of delivery vehicle, the type of copper-containing agent, the desired delivery duration, etc. For example, depending on the how the composition is formulated, the composition can include an amount of copper from about 0.0001 mg/ml to about 5 mg/ml or about 50 mg/ml. In other examples, the composition can include an amount of copper from about 0.0005 mg/ml to about 0.03 mg/ml, from about 0.01 mg/ml to about 5 mg/ml, or from about 0.001 to about 0.005 mg/ml. In some additional examples, the composition can include an amount of copper from about 0.0001 mg/ml to about 0.05 mg/ml, about 0.00025 mg/ml to about 0.015, about 0.0005 mg/ml to about 0.00075 mg/ml, or about 0.0008 mg/ml to about 0.0011 mg/ml. Thus, in some examples, the therapeutically effective amount can be defined as the amount of copper included in the composition. For example, an amount of 0.0016 mg/ml of copper (II) sulfate, anhydrous, provides the composition with a copper content of about 0.00064 mg/ml copper. This is because the molecular weight of copper (II) sulfate is about 159.6 g/mol, but only about 63.5 g/mol or about 40% of the agent is copper itself. Thus, the therapeutically effective amount can be determined based on the copper content provided by the copper-containing agent rather than the amount of copper-containing agent itself. As an alternative example, an amount of 0.0018 mg/ml of copper (II) acetate, anhydrous, provides the composition with a copper content of about 0.00063 mg/ml.

Alternatively, the therapeutically effective amount can be defined as a wt % of the copper-containing agent in the composition. Again, depending on how the composition is formulated, the therapeutically effective amount of the copper-containing agent can be an amount from about 0.00005 wt % to about 5 wt %, 10 wt %, or 15 wt %. In some examples, the therapeutically effective amount of the copper containing agent can be from about 0.05 wt % to about 15 wt %, from about 0.01 wt % to about 10 wt %, or from about 0.005 wt % to about 5 wt %. In other examples, the therapeutically effective amount of the copper-containing agent can be an amount from about 0.0001 wt % to about 0.0005 wt %, from about 0.0001 wt % to about 0.0002 wt %, from about 0.0002 wt % to about 0.0003 wt %, or from about 0.0003 wt % to about 0.0004 wt %. In yet other examples, the therapeutically effective amount of the copper-containing agent can be an amount from about 0.001 wt % to about 0.01 wt % or about 0.003 wt % to about 0.008 wt %. In yet other examples, the therapeutically effective amount of the copper-containing agent can be an amount from about 0.01 wt % to about 0.1 wt %, or from about 0.03 wt % to about 0.08 wt %. It is noted that these weight percentages are calculated based on copper (II) sulfate, anhydrous. Thus, where an alternative copper-containing agent is employed, the weight percentages can be converted accordingly.

However, a particular amount of copper-containing agent in the composition does not necessarily mean that all of the copper content will be bioavailable upon administration. The bioavailability of the copper can vary to some extent from one copper-containing component to another, as well as pH and other compositional factors. Thus, the therapeutically effective amount of copper-containing agent can also be adjusted based on the bioavailability of copper with respect to a particular copper carrier, pH, formulation, or the like.

The copper-containing agent can also be administered with a therapeutically effective amount of a second active or therapeutic agent. Such additional agents can include riboflavin, rose bengal, hydroxylysine, the like, or combinations thereof. Additionally, a plurality of different cross-linking agents can be administered concurrently, such as a plurality of different copper-containing agents, or a copper-containing agent in combination with another non-copper-containing cross-linking agent such as a zinc-containing agent, magnesium-containing agent, iron-containing agent, or silver-containing agent, for example.

The copper-containing agent can be provided in a pharmaceutically acceptable carrier. The pharmaceutically acceptable carrier can be formulated in a variety of ways to deliver the copper-containing agent. Non-limiting examples can include solutions, suspensions, gels, hydrogels, thermo-responsive gels, subconjunctival injections, depots, films, contact lenses, pledgets, or the like. In one specific example, the formulation can be an ophthalmic drop. In some examples, the composition can be formulated as a copper-eluting contact lens, such as a soft lens, a toric lens, a hard lens, a scleral lens, the like, or combination thereof.

Depending on how the composition is formulated, the pharmaceutically acceptable carrier can include a variety of excipients. For example, a pharmaceutically acceptable carrier can include a solubilizing agent, a tonicity agent, a pH adjuster, a thickener or gelling agent, a polymer or polymeric matrix, a preservative, water, the like, and combinations thereof.

Non-limiting examples of solubilizing agents can include phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, BSS Plus, Ringer's lactate solution, normal saline (i.e. 0.9% saline), ½ normal saline, the like, or combinations thereof. Solubilizing agents can be present in the pharmaceutically acceptable carrier in various amounts. In one aspect, the solubilizing agent can have a concentration in the carrier of from about 10 wt %, about 20 wt %, about 30 wt %, about 40 wt %, or about 50 wt % to about 80 wt %, about 90 wt %, about 95 wt %, about 97 wt %, about 99 wt %, or about 99.9999 wt %.

Non-limiting examples of tonicity agents can include the solubilizing agents previously listed, as well as sodium chloride, potassium chloride, calcium chloride, magnesium chloride, mannitol, sorbitol, dextrose, glycerin, propylene glycol, ethanol, trehalose, the like, or combinations thereof. The tonicity agent can be used to provide an appropriate tonicity of the formulation. In one aspect, the tonicity of the formulation is from about 250 to about 350 milliosmoles/liter (mOsm/L). In another aspect, the tonicity of the formulation is from about 270 to about 330 mOsm/L. Tonicity agents can be present in the pharmaceutically acceptable carrier in various amounts. In one aspect, the tonicity agent can have a concentration in the carrier of from about 0.1 wt %, about 0.5 wt %, or about 1 wt % to about, 2 wt %, about 5 wt %, or about 10 wt %.

Non-limiting examples of pH adjusters can include a number of acids, bases, and combinations thereof, such as hydrochloric acid, phosphoric acid, citric acid, sodium hydroxide, potassium hydroxide, calcium hydroxide, and the like. The pH adjusters can be used to provide an appropriate pH for the formulation. In one aspect, the pH can be from about 5.5 to about 8.5. In one aspect, the pH can be from about 5.8 to about 7.8. In another aspect, the pH can be from about 6.5 to about 7.8. In yet other examples, the pH can be from about 7.0 to about 7.6. pH adjusters can be present in the pharmaceutically acceptable carrier in various amounts. In one aspect, the pH adjuster can have a concentration in the carrier of from about 0.01 wt %, about 0.05 wt %, about 0.1 wt %, or about 0.5 wt % to about 1 wt %, about 2 wt %, about 5 wt %, or about 10 wt %.

Non-limiting examples of thickeners or gelling agents can include glycerol, propylene glycol, polyethylene glycol, polyvinyl alcohol, cellulose derivatives (such as methyl cellulose, carboxymethyl cellulose, hydroxypropyl cellulose, and the like) ethylvinyl alcohol, hyaluronic acid, the like, or combinations thereof. Thickeners or gelling agents can be present in the pharmaceutically acceptable carrier in various amounts. In one aspect, the thickener or gelling agent can have a concentration in the carrier of from about 0.01 wt %, about 0.05 wt %, about 0.1 wt %, or about 0.5 wt % to about 2 wt %, about 8 wt %, about 15 wt %, or about 30 wt %.

Non-limiting examples of polymers that can be used to prepare a polymer matrix for a film, contact lens or the like, can include biodegradable or non-biodegradable polymers. Non-limiting examples of polymers or polymer combinations can include poly(methylmethacrylate), hydroxyethylmethacrylate, polysiloxanes, poly(lactic-co-glycolic acid) (different ratios of lactic to glycolide content and end groups such as acid or ester termination), polyvinyl alcohol, polyvinyl acetate, ethylene vinyl acetate, polyethylene glycol, polylactic acid, polyglycolic acid, hydroxypropyl methylcellulose, hydroxypropylcellulose, carboxymethylcellulose, croscarmellose, polycaprolactone, hyaluronic acid, albumin, sodium chloride block copolymers thereof, salts thereof, the like, or combinations thereof. Specific copolymers such as polylactic-polyglycolic acid block copolymers (PLGA), polyglycolic acid-polyvinyl alcohol block copolymers (PGA/PVA), hydroxypropylmethylcellulose (HPMC), polycaprolactone-polyethylene glycol block copolymers, croscarmellose, and the like can be particularly effective for biodegradable matrixes, where desirable.

In some examples, the composition can include thermo-responsive polymers. Non-limiting examples of thermo-responsive polymers can include poly(N-isopropyl acrylamide), poly [2-(dimethylamino)ethylmethacrylate], hydroxypropylcellulose, poly(vinyl caprolactame), polyvinyl methyl ether, polyethylene oxide, polyhydroxyethylmethacrylate, ABCBA-type pentablock polymers, chitosan, the like, or combinations thereof. Such thermo-responsive polymers can bind or can be functionalized to bind a particular copper-containing agent within a range of temperatures and release the copper-containing agent upon changing the temperature of the surrounding environment, such as placing the composition in contact with the eye, applying a heat source to the eye after administration of the composition, or the like.

Non-limiting examples of preservatives can include benzalkonium chloride (BAK), cetrimonium, sodium perborate, ethylenediaminetetraaceticacid (EDTA) and its various salt forms, chlorobutanol, and the like. Preservatives can be present in the pharmaceutically acceptable carrier in various amounts. In one aspect, the preservative can have a concentration in the carrier of from about 0.001 wt %, about 0.005 wt %, about 0.01 wt %, or about 0.05 wt % to about 0.1 wt %, about 0.25 wt %, about 0.5 wt %, or about 1 wt %.

In one specific example, the pharmaceutically acceptable carrier can be formulated as an ophthalmic drop and can include BSS in an amount from about 50 wt % to about 99.9999 wt %. In another specific example, the pharmaceutically acceptable carrier can be formulated as an ophthalmic drop and can include artificial tears (i.e. Refresh Tears®, Genteal®, Oasis Tears®, and the like).

Regardless of how the ophthalmic composition is formulated, the ophthalmic composition can be used as an ophthalmic dosage form to administer a therapeutically effective dose of the copper-containing agent. In some examples, the ophthalmic dosage form can provide from about 0.0005 µg to about 0.5 µg of copper per administration event. In yet other examples, the ophthalmic dosage form can provide from about 0.006 µg to about 0.06 µg, about 0.01 µg to about 0.03 µg, or about 0.016 µg to about 0.044 µg of copper per administration event. In yet other examples, the ophthalmic dosage form can provide from about 0.0005 µg to about 5 µg of copper per day. In yet other examples, the ophthalmic dosage form can provide from about 0.001 µg to about 2 µg, about 0.006 µg to about 0.24 µg, about 0.01 µg to about 0.12 µg, or about 0.016 µg to about 0.18 µg of copper per day. It is noted that not all of the copper that is provided by the dosage form is necessarily bioavailable, but in some examples it can be.

In some examples, the ophthalmic dosage form can be used in an effective dosage regimen to provide a therapeutically effective amount of the copper-containing agent. The effective dosage regimen can include administering the ophthalmic dosage form once per day, twice per day, three times per day, four times per day, or more.

In yet other examples, the ophthalmic dosage form can be formulated to biodegrade and provide controlled and sustained release of the copper-containing agent over a predetermined period of time. In yet other examples, the ophthalmic dosage form can be formulated to release the copper-containing agent from a non-biodegradable matrix in a controlled and sustained manner. In examples such as these, the dosage form can be formulated to release the copper-containing agent over a period of hours, days, or weeks, as desired. In some specific examples, the dosage form can be formulated to deliver from about 0.005 mcg of copper to about 250 mcg of copper per week. In yet other examples, the dosage form can be formulated to deliver from about 0.008 mcg to about 200 mcg per week, about 0.01 mcg to about 150 mcg per week, or about 0.1 mcg to about 100 mcg per week. Further, the dosage form can typically be formulated to have zero-order drug release kinetics.

The dosage form can be held in or stored in the container as a pre-mixed composition that is ready to administer without further dilution or preparation. In some embodiments, a single container can hold a volume or amount of the composition that is adequate for a single dose. In yet other examples, a single container can hold a volume or amount of the composition that is adequate for multiple doses.

A number of suitable containers can be used. In one aspect, the container can be an amber-colored container. In some examples, the container can be made of glass, polypropylene, polyethylene, polycarbonate, polyvinylchloride, the like, or a combination thereof. In some examples, the container can have a volume of from about 0.5 ml to about 50 ml. In another aspect, the container can have a volume of from about 1 ml to about 30 ml, about 5 ml to about 20 ml, or about 3 ml to about 15 ml. In one aspect, the container can hold a single dose of the therapeutic composition or dosage form. In another aspect, the container can hold a plurality of doses of the therapeutic composition or dosage form.

In some examples, about 0.005 mg to about 1 mg of the copper-containing agent can be included in the container. In yet other examples, about 0.01 mg to about 0.5 mg of the copper-containing agent can be included in the container. In some examples, about 0.001 mg to about 0.5 mg of copper can be included in the container. In some examples, about 0.005 mg to about 0.2 mg of copper can be included in the container.

In some specific examples, the dosage form can be a topical ophthalmic dosage form that is formulated as an eye drop and carried in a container adapted to dispense the composition in a drop-wise manner at a drop volume of from about 5 µl to about 50 µl. Where the composition is formulated as an eye drop, in some examples, the container can include a fitted nozzle or tip from which the composition can be dispensed. As such, the container can typically be collapsible to dispense the composition. However, in some cases, after the composition is dispensed, air can be sucked back into the container, which can contaminate the composition. In some examples, the nozzle or tip can include a valve mechanism, filter, the like, or combination thereof to prevent or minimize introduction of bacteria and other contaminants into the container. Additionally, as previously discussed, the container can be adapted to dispense the ophthalmic composition in a drop-wise manner. For example, the container can be adapted to dispense the ophthalmic composition at a drop volume of from about 5 µl to about 50 µl, such as about 15 µl, about 20 about 25 about 30 about 35 µl, about 40 about 45 or about 50 µl. In some specific examples, the drop volume can be from about 15 µl to about 40 about 5 µl to about 30 about 20 µl to about 30 about 25 µl to about 35 or about 30 µl to about 40 µl.

Further included with dosage form can be an administration mechanism, such as a syringe, a dropper, or other mechanism. In additional embodiments, suitable packaging can be used to provide the composition, container, and instructions for the use thereof, and optionally an administration mechanism in a single integrated system.

The compositions or dosage forms described herein can also be employed in a method of treating an ophthalmic condition. Such a method can include administering a therapeutically effective amount of the composition or dosage form to an eye of a subject during a treatment period. The method can be used to treat any of the conditions previously mentioned herein and other similar ophthalmic conditions.

In one example, the composition or dosage form can be administered at from 1 to 4 time points per day per eye in need thereof. The dosage amount at each time point can be from about 5 µl to about 50 µl, about 5 µl to about 30 about 20 µl to about 30 about 25 µl to about 35 or about 30 µl to about 40 µl.

The treatment period can depend on a number of factors, such as the type and severity of the condition, the age of the subject at diagnosis, and the like. Typically, the treatment period can be from about 1 month to chronic treatment, depending on the circumstances. For example, in some cases, a young child can receive chronic treatment, whereas older children and teenagers (e.g. ages 10-18) can receive treatment from two to three years, a young adult (e.g. ages 18-30) can receive treatment from one to two years, and an adult aged 30 years or older can receive treatment from about six months to one year. Thus, in some examples, the treatment period can be from about 1 month to chronic treatment. In yet other examples, the treatment period can be from about 1 month, about 3 months, or about 6 months to about 12 months, about 18 months, about 24 months, about 30 months, about 36 months, or until the condition has been satisfactorily resolved.

In some examples, the ophthalmic composition can be administered as an ophthalmic drop. In yet other examples, the ophthalmic composition can be administered as a subconjuntival injection. In yet other examples, the ophthalmic composition can be administered in the form of a topical film or contact lens. In some examples, the topical film or contact lens can be configured to biodegrade over time to provide controlled and sustained release of the copper-containing agent.

Generally, the methods described herein can increase collagen cross-linking in the cornea as compared to an untreated eye. More specifically, the method can increase lysinonorleucine cross-linking density, histidinyl-hydroxylysinonorleucine cross-linking density, or both, as well as other collagen cross-links associated with the cornea as compared to an untreated eye. Further, the methods described herein can decrease the radial strain of the cornea by at least about 10%, 25%, or 50% as compared to the cornea without treatment. Additionally, the methods described herein can decrease corneal diopter of a keratoconus cornea as compared to an untreated keratoconus cornea.

EXAMPLES

Example 1—Copper-Containing Active Agents can Increase Corneal Lysyl Oxidase Activity Cultured corneal stroma cells from normal and keratoconus corneas (n=3 each) in 10% FBS DMEM were either exposed to BSS control or 0.0016 mg/mL $CuSO_4$ in balanced salt solution (BSS) then filtered through a 0.25µ filter.

Conditioned culture medium underwent a peroxidase-coupled fluorometric activity assay for LOX.

Tissues were collected under sterile techniques in an operative setting. Tissue samples were stored in a 10 cm tissue culture dish in an Optisol solution. Corneal tissue was suspended in 15% fetal bovine serum (FBS) DMEM/F12 with penicillin/streptomycin. Epithelium and Descemet's membrane were removed mechanically under a stereo microscope. The sample was further cut into small pieces by a surgical scissor, and added to 1 mg/mL collagenase; 10 mL per cornea was used. The sample pieces were plated to a 10 cm tissue culture dish and placed in a tissue culture incubator at 37° C. with 5% $CO_2$. After 5 days, the cells were harvested and plated in 10% FBS DMEM without phenol red.

LOX enzyme activity in culture medium was measured using a peroxidase-coupled fluorometric assay using Amplex red. Briefly, the corneal stroma cells were plated to 6 well plate at $0.2 \times 10^{\wedge}6$ cells with 2 mL culture medium. After 3 days, the culture was harvested for LOX enzyme activity assay. 50 uL of each culture medium was placed in a black 96 well plate. Then, 50 uL of 2× assay buffer (2.4 M urea, 100 mM sodium borate (pH 8.2), 20 mM 1,5-diaminopentane, 20 uM Amplex red and 2 unit/mL Horseradish peroxidase). As a parallel assay, we added 500 uM aminopropionitrile (BAPN) which can diminish LOX activity completely. The fluorescence of oxidized Amplex red was recorded every 10 minutes using fluorescence plate reader. After subtracting the background fluorescence, the fluorescence intensity was plotted against the incubation time (FIGS. 1A and 1B).

Figure 1A:
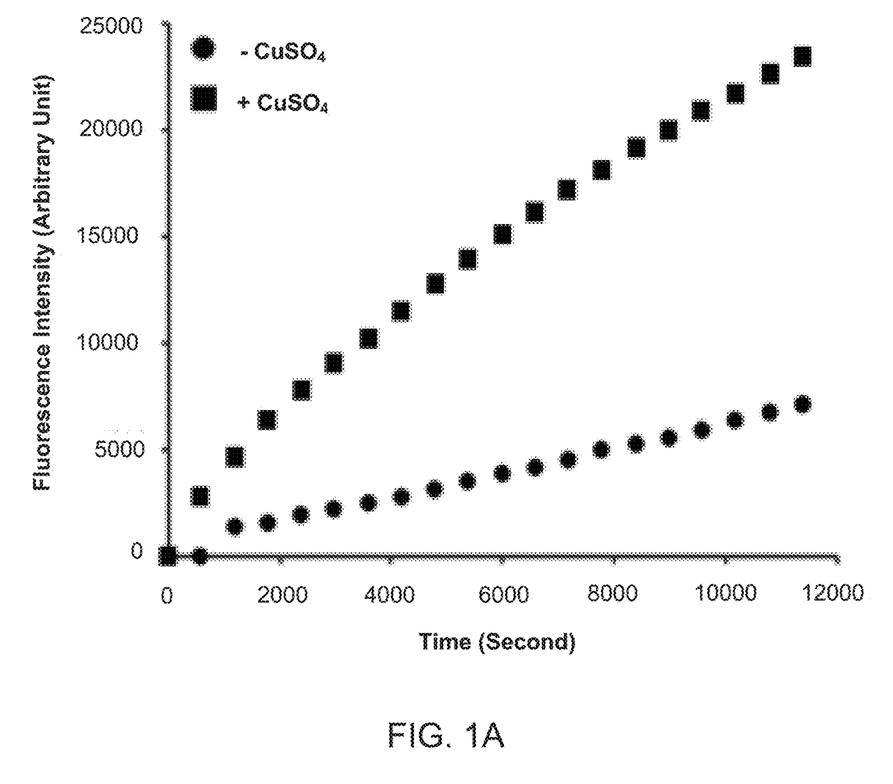
FIG. 1A is a graph showing increased lysyl oxidase activity in corneal fibroblast cells in response to Cu treatment.
Figure 1B:
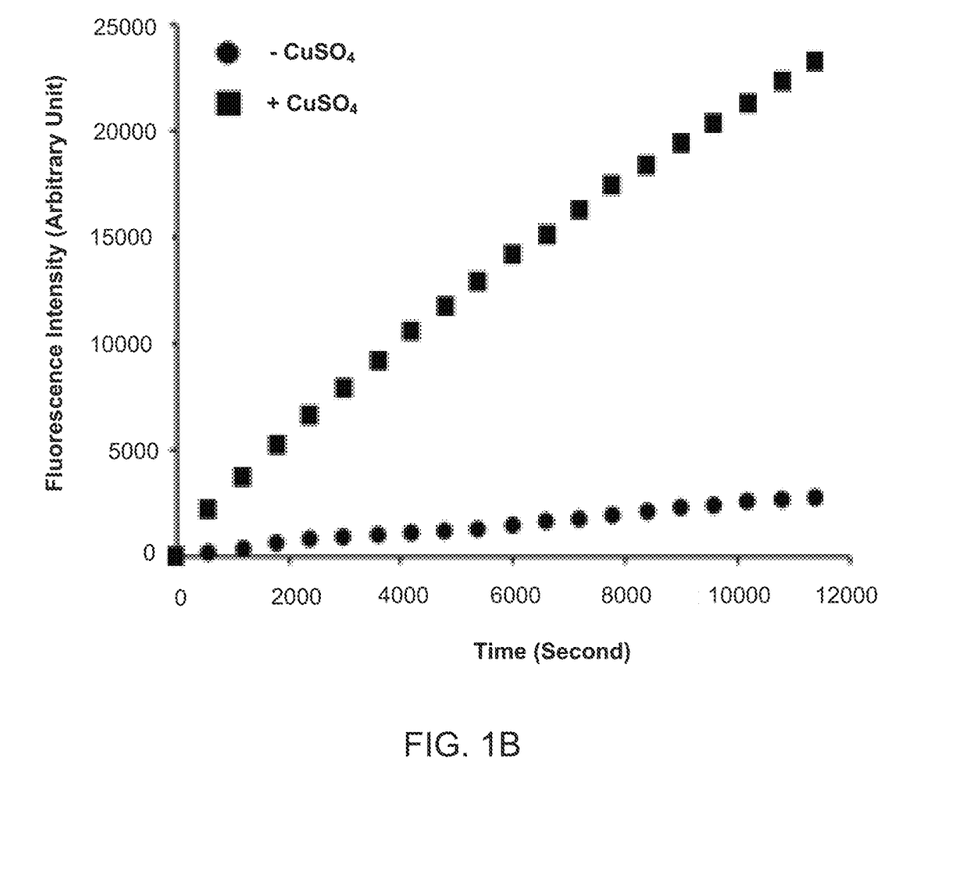
FIG. 1B is another graph showing increased lysyl oxidase activity in corneal fibroblast cells in response to Cu treatment.

Based on the peroxidase-coupled fluorometric lox activity assay, and as illustrated in FIGS. 1A-1B, it can be seen that copper dramatically increased lox enzyme activity in normal and keratoconus corneal fibroblast cells. This indicated that copper has the potential to increase collagen cross-linking by enhancing lox activity in keratoconus cornea.

Example 2—Copper-Containing Active Agents can Increase Collagen Cross-Linking in the Cornea Sample Preparation:

Each Human Keratoconus Cornea was bisected. One half was treated with 0.0016 mg/ml CuSo4 in Optisol solution for 1 week and other half was left untreated. After one week each cornea was kept in negative 80° C. for future analysis.

Sample Extraction:

The cornea samples were washed with PBS pH 7.4 and powdered in liquid nitrogen and pulverized with a Freezer Mill. Cornea samples were demineralized with 0.5 M EDTA in 0.05 M Tris buffer, pH 7.4, for 48 h at 4° C. The insoluble fraction was washed twice with distilled water by centrifugation at 5000 g at 47 C for 20 min and lyophilized. The lyophilized sample was hydrolyzed with constantly boiling redistilled 6 N HCl in vacuo for 24 h at 110° C. The hydrolysate was neutralized with 2.5 N NaOH and dissolved in distilled water. Analyses were performed for Lysinonorleucine (LNL) and Histidinohydroxylysinonorleucine (HHL) separately by HPLC.

HPLC Method for Lysinonorleucine (LNL):

Amino acid analysis is an important application area in protein chemistry and food analysis. Many different applications exist in this field. Automated pre-column derivatization followed by reverse phase LC has become a useful procedure for efficient analysis, since it is an easy and simple to use technique. An Agilent 1290 Infinity LC System was used with automated pre-column derivatization for fast and sensitive analysis of Lysinonorleucine (LNL). The column used for this method is Agilent ZORBAX Eclipse Plus RRHD C18 (3.0 mm×50 mm, 1.8 µm) and Mobile phase consisted of Solvent A: 10 mM disodium phosphate+10 mM sodium tetraborate pH 8.2 and Solvent B: ACN/MeOH/H2O (45:45:10)

HPLC Method for Histidinohydroxylysinonorleucine (HHL):

To 25 ml of the protein hydrolysate sample (less than 3 mM as the total amino acid concentration), 50 µl of 1.5 mM Ne-methyl-L-lysine hydrochlo ide (Mly) in 0.26 M borate buffer, pH 9.5, and 50 µl of acetone were added in a 1.5-ml reaction vial. Then 25 µl of FMOC-Cl reagent (6 mM FMOC-Cl in acetone) was added and the mixture was allowed to react for 2 min at room temperature. The reaction mixture was extracted twice with 350 ml of pentane to remove excess FMOC-Cl reagent. The aqueous phase was subjected to chromatography.

Figure 2A:
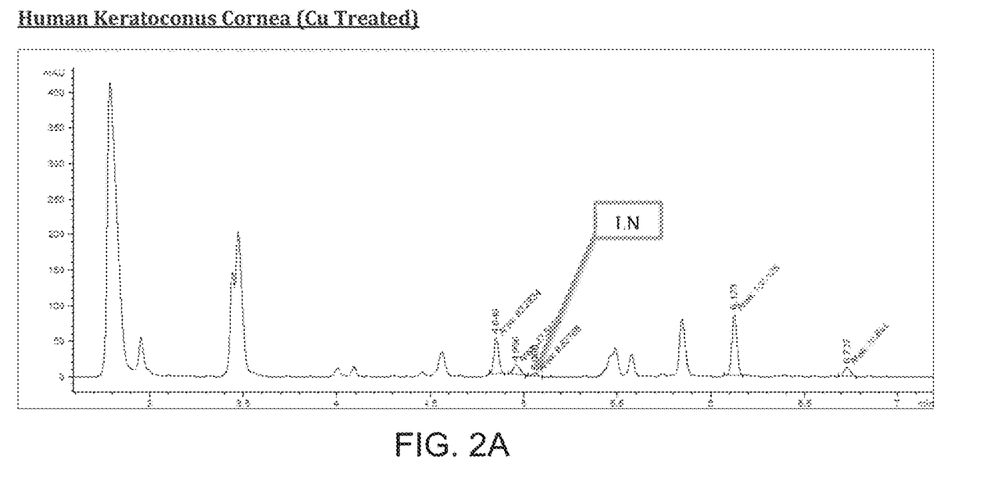
FIG. 2A illustrates a chromatograph showing increased lysinonorleucine cross-linking in a keratoconus cornea in response to Cu treatment.
Figure 2B:
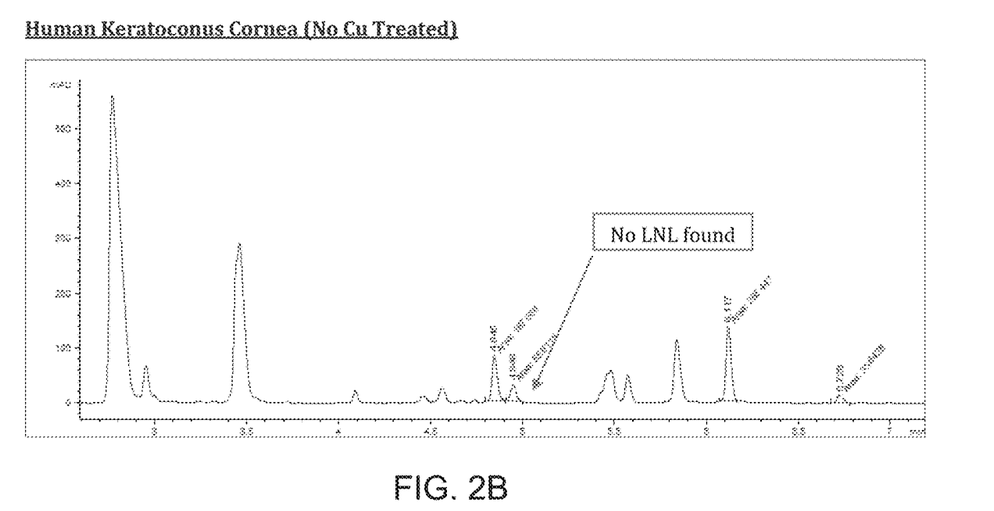
FIG. 2B illustrates a chromatograph showing no detectable lysinonorleucine cross-linking in an untreated keratoconus cornea.
Figure 2C:
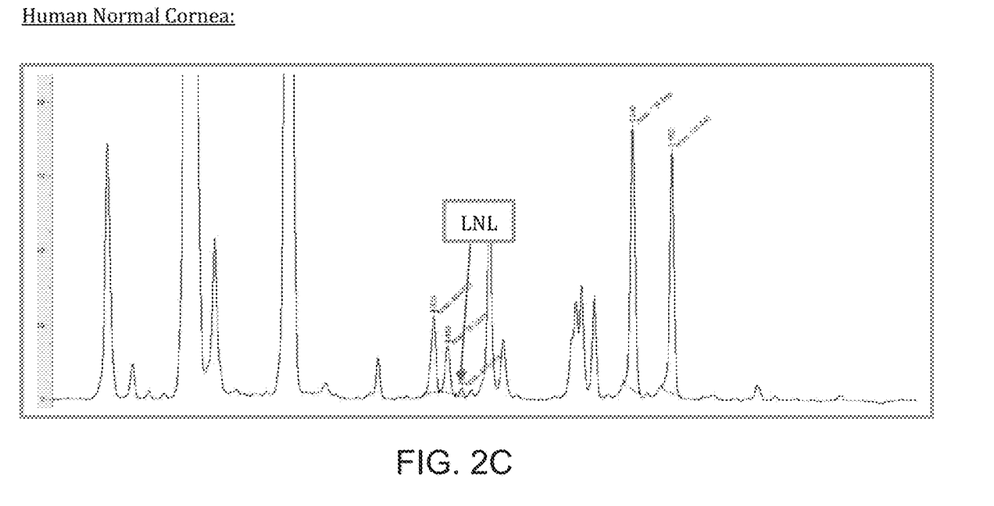
FIG. 2C illustrates a chromatograph showing lysinonorleucine cross-linking in a normal cornea.

Cornea cross-linking is tissue specific. The predominant cross-links generated in the human cornea are lysinonorleucine (LNL). LNL are the building blocks for subsequent multivalent cross-links such as the histidinyl-hydroxylysinonorleucine (HHL). Normal and keratoconic human corneas were treated for 1 week with 0.0016 mg/ml $CuSO_4$. Then, an HPLC analysis was performed to measure levels of LNL (FIGS. 2A-2C) and HHL (FIGS. 3A-3C).

Indeed, a significant increase in LNL and HHL levels in the copper treated corneas was observed. As illustrated in FIG. 2A, LNL cross-links were observed in human keratoconus corneas treated with $CuSO_4$, as described above. In contrast, as illustrated in FIG. 2B, no LNL cross-links were observed in keratoconus corneas that were not treated with $CuSO_4$. FIG. 2C illustrates that LNL cross-links are also present in normal corneas.

Figure 3A:
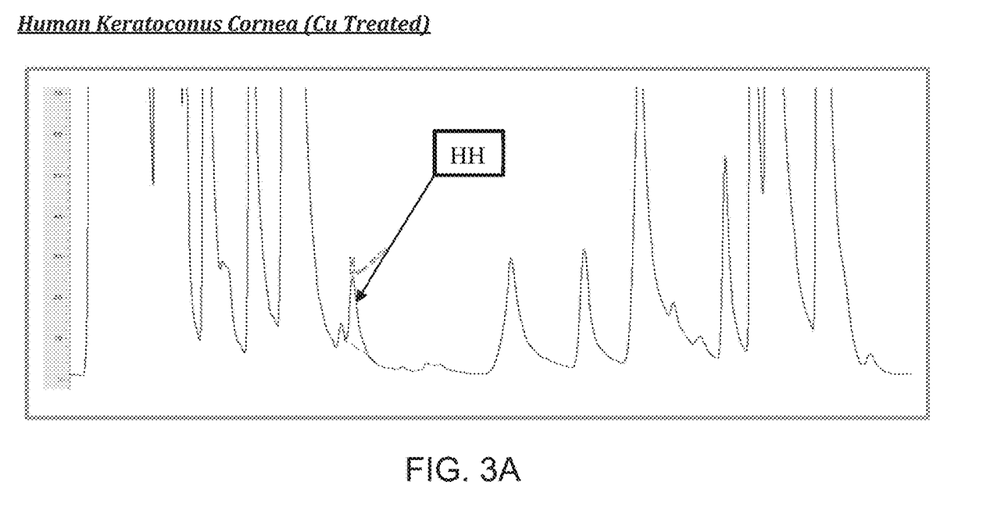
FIG. 3A illustrates a chromatograph showing increased histidino-hydroxylysinonorleucine cross-linking in a keratoconus cornea in response to Cu treatment.
Figure 3B:
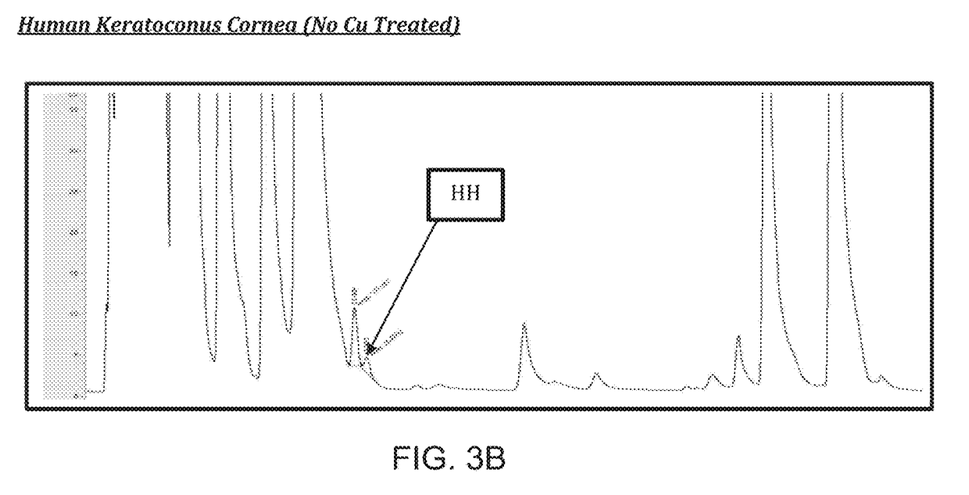
FIG. 3B illustrates a chromatograph showing minimal histidino-hydroxylysinonorleucine cross-linking in an untreated keratoconus cornea.
Figure 3C:
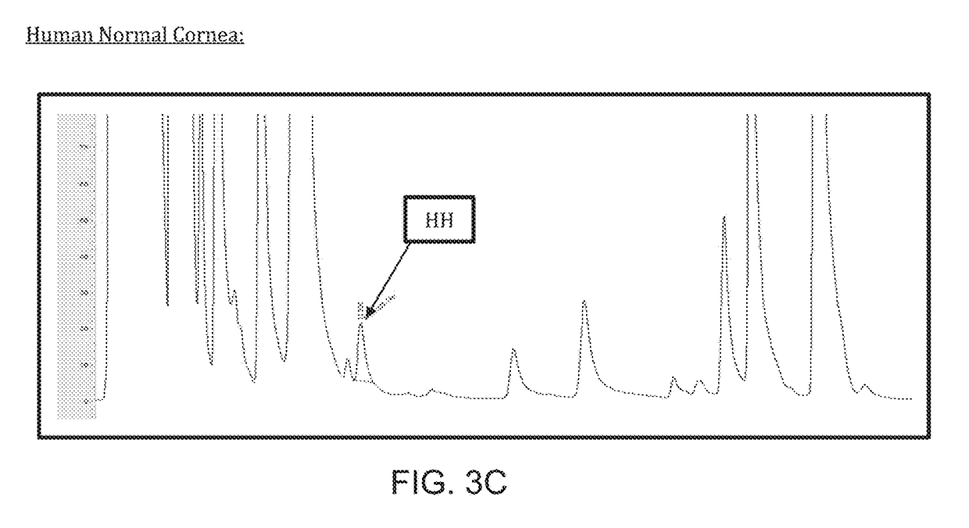
FIG. 3C illustrates a chromatograph showing histidino-hydroxylysinonorleucine cross-linking in a normal cornea.

Similarly, as illustrated in FIG. 3A, HHL cross-links are also observed in human keratoconus corneas treated with $CuSO_4$, as described above. In contrast, as illustrated in FIG. 3B, negligible levels of HHL cross-links were observed in keratoconus corneas that were not treated with $CuSO_4$. FIG. 3C illustrates that HHL cross-links in normal corneas are at higher levels than those observed in keratoconus cornease that were not treated with $CuSO_4$.

Thus, $CuSO_4$ treatment clearly provided an increase in both LNL and HHL cross-linking in keratoconus corneas.

Example 3—Treatment with a Copper-Containing Agent Increases Corneal Strength

Cornea radial strain measurements were performed on human cadaver corneas and on rabbit corneas. Human cadaver corneas (n=2 pairs) were cultured as previously mentioned in Example 1. The treated group was immersed in 0.0016 mg/ml $CuSO_4$ for 2 weeks. The samples also contained a small portion of sclera at both ends. Mineral oil was applied on the surface of the sclera-cornea-sclera strip to minimize tissue dehydration. Rabbit corneas were divided into 4 groups. Two groups were treatment groups receiving either $CuSO_4$ 0.0025 mg/ml three times per day or $CuSO_4$ 0.0025 mg/ml once per day. Two groups served as control receiving only BSS.

The sample was coupled between a motor and a transducer that applied a controlled pressure from 5-30 mmHg and measured the resultant radial strain. The sample length between the two gripping jaws was approximately 10 mm. Sample geometric information, including width and thickness, was input into the Rheometrics System Analyzer (RSA) control panel. Sample thickness was measured by an ultrasound pachymeter (DGH 550 Pa-chette2; DGH Technology, Exton, Pa.).

Figure 4:
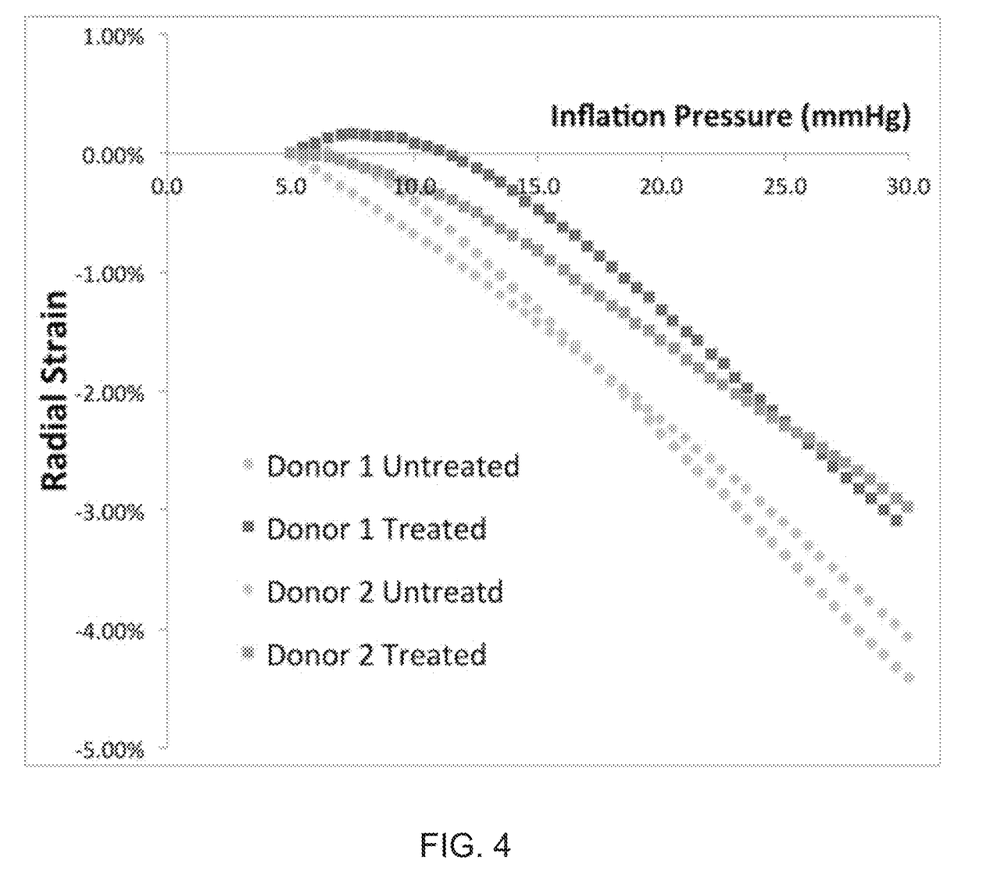
FIG. 4 is a graph showing increased corneal strength in response to Cu treatment.
Figure 5:
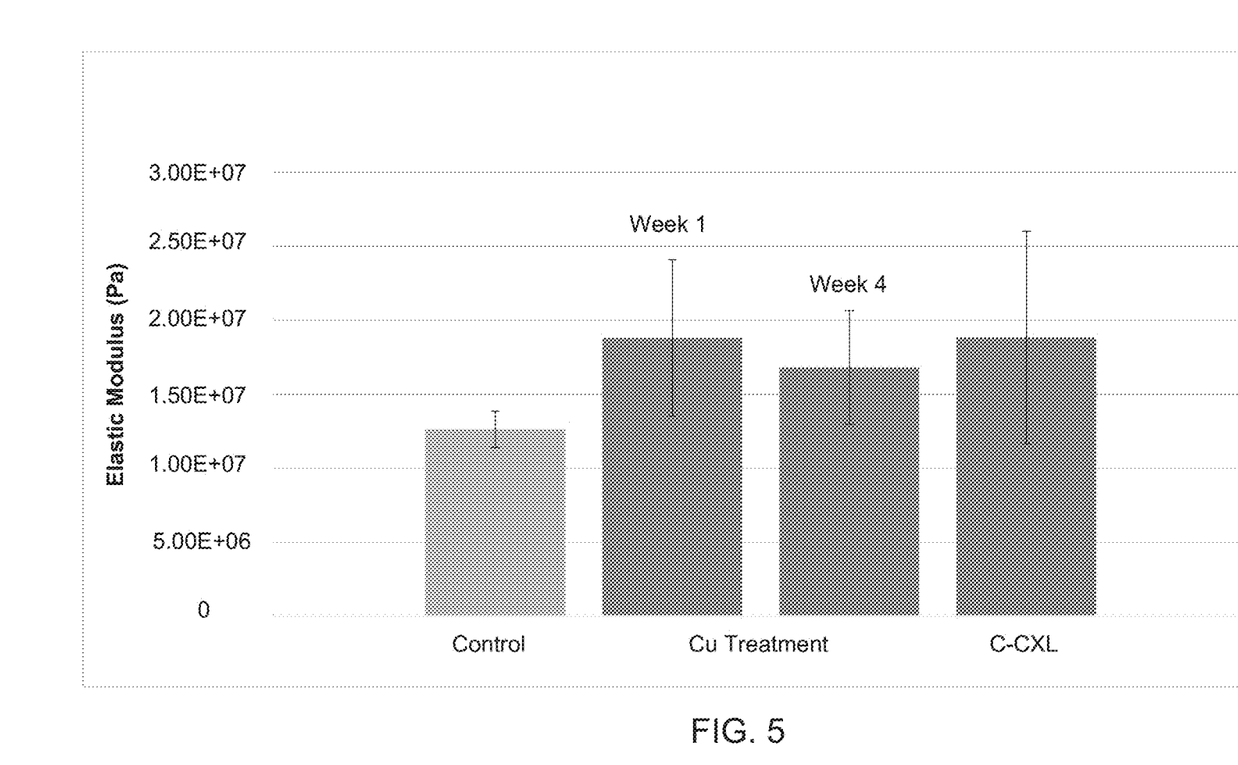
FIG. 5 is a chart showing improved corneal biomechanics in response to Cu treatment.

The results show a marked increase in stiffness and decrease in radial strain after copper sulfate treatment (FIG. 4). The average peak radial strain induced by ocular pulse at 20 mmHg in treated corneas was about 1.5 times lower than that in untreated corneas. This represents about a 50% increase in corneal strength, demonstrating that cross-linking results in a stiffer corneal response. Further, as illustrated in FIG. 5, treatment with $CuSO_4$ also provided corneal biomechanics comparable to that seen with laser cross-linking.

Example 4—Rabbit Corneal Topography

Corneal curvature of specific areas was monitored by corneal topography, which displays results in dioptric values. Copper sulfate ($CuSO_4$) at 0.0025 mg/ml was administered to New Zealand white rabbits at a dose of once per day and three times per day. Additionally, a high concentration sample of 0.025 mg/ml was administered to New Zealand with rabbits once per day during the treatment period. Three different controls were administered either no drops, BSS, or artificial tears. Each of the 6 groups included 6 test subjects each. Topography images were taken before treatment and weekly for 5 weeks. Diopter measurements were the mean K values and at 3 mm. These values were compared to diopter measurements in laser cross-linked corneas after 1 month and 1 year.

Figure 6:
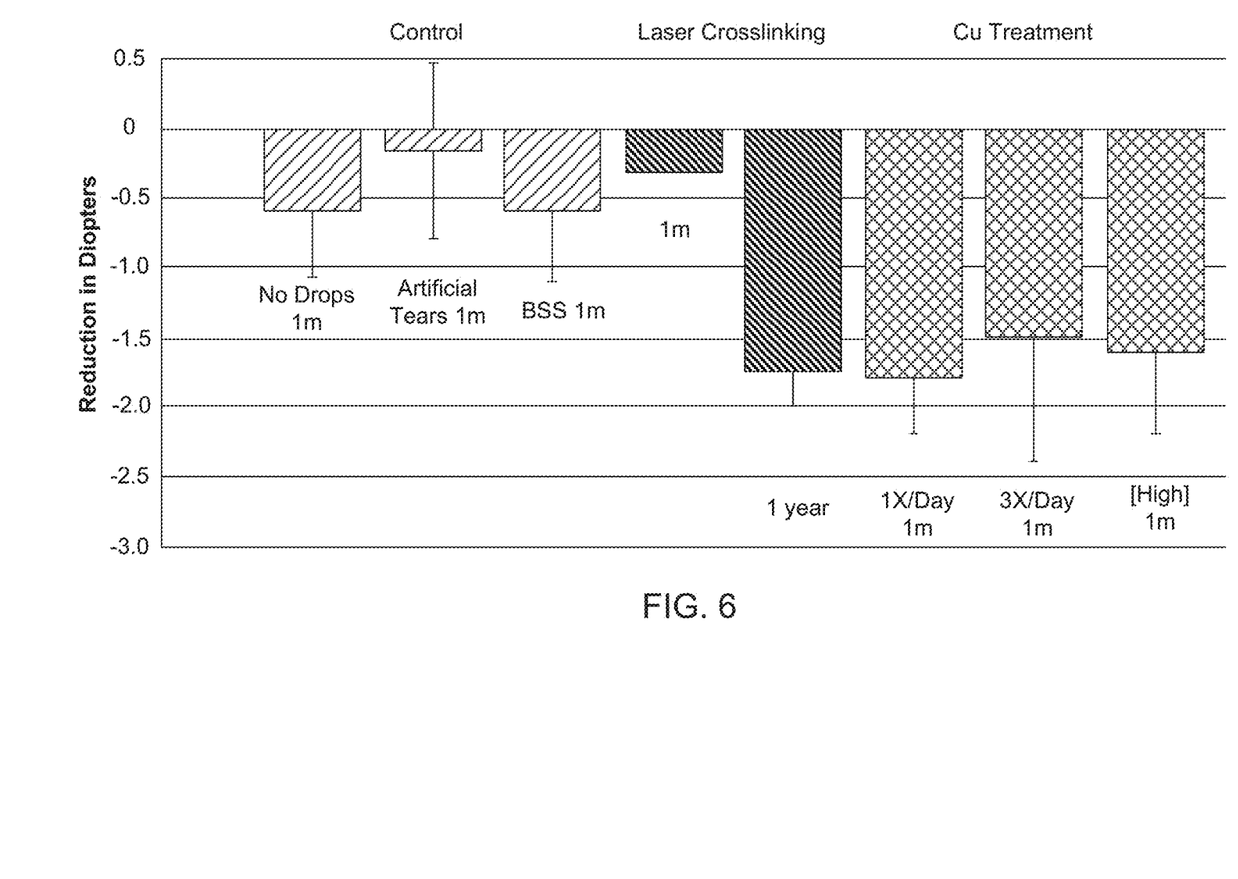
FIG. 6 is a chart showing decreased corneal diopter measurements in response to Cu treatment.

As can be seen in FIG. 6, there was a greater decrease in diopter measurements in the treatment groups as compared to the control groups. Further, 1 month of treatment with $CuSO_4$ provided similar diopter measurements as those observed in laser cross-linked corneas after 1 year.

Example 5—Safety of Copper Eye Drops In Vivo

Copper sulfate ($CuSO_4$) solution was prepared at a concentration of 0.0025 mg/ml and administered three times a day (TID) or once a day (QD) to rabbits. An anterior segment evaluation was performed with slit-lamp biomicroscopy and Heidelberg Spectralis anterior segment optical coherence tomography (AS-OCT). Two rabbits (n=4 eyes) were sacrificed at each of day 1, week 1, week 4, and week 6 for copper levels in eye tissues and compared to control (no drops) rabbits. Aqueous humor, vitreous, retina, cornea, lens, and blood samples were analyzed for copper ions using inductively coupled plasma mass spectrometry (ICP-MS).

Rabbits (n=2) were sacrificed after 42 days by intravenous injection of 0.3 ml/kg euthanasia solution and the eyes were enucleated for histological evaluations and reading for signs of inflammation, tissue damage, scarring and fibrosis. The anterior section of the eyes were fixed in 10% formaldehyde-glutaraldehyde solution, dehydrated in a graded series of alcohol, embedded in paraffin, and sectioned with a microtome. The sections were stained with appropriate staining (hematoxylin and eosin and Masson Trichrome).

Figure 7A:
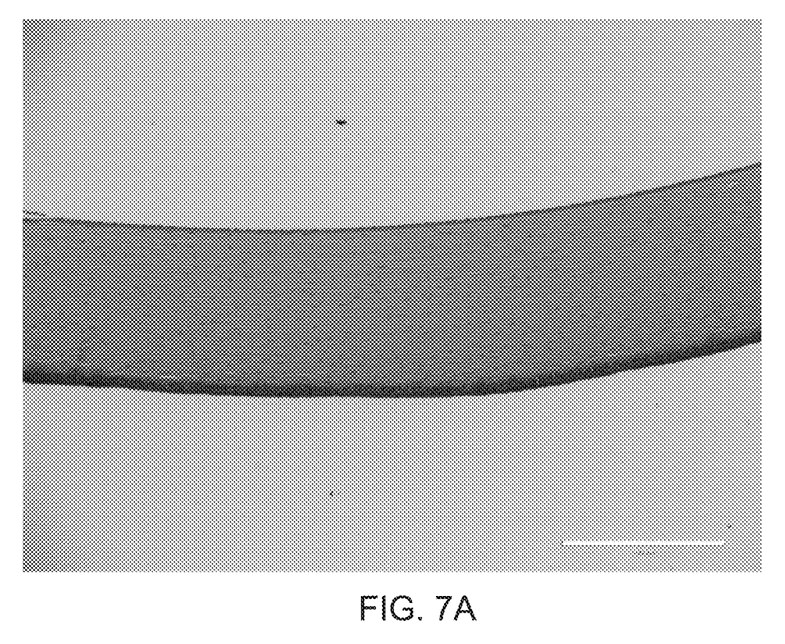
FIG. 7A illustrates an image of a stained cornea after 6 weeks of Cu treatment.
Figure 7B:
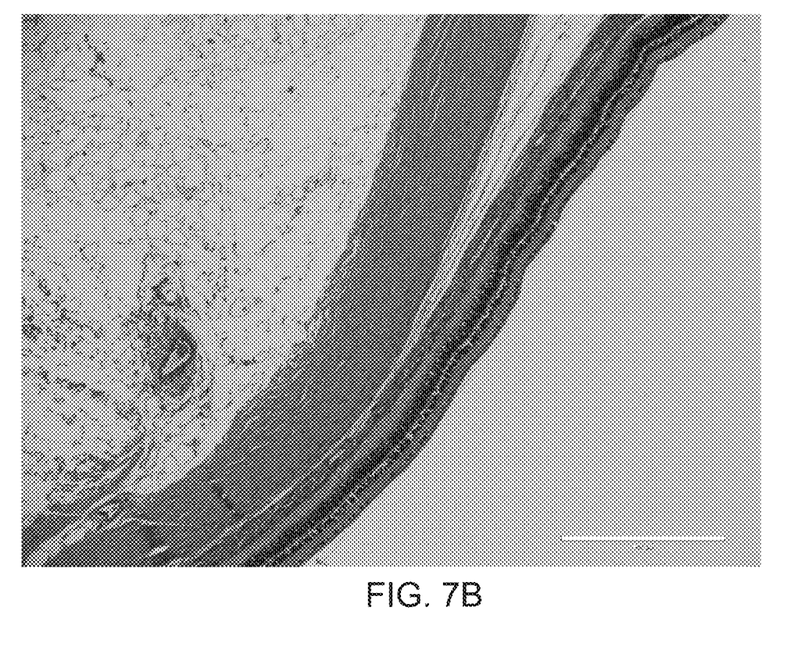
FIG. 7B illustrates an image of a stained retina/choroid after 6 weeks of Cu treatment.

There was no effect on electroretinography (ERG) measurements due to treatment with Cu. Further, there was no observed toxicity in any of the dissected eye tissues. Additionally, there was no observed corneal haze, whereas the laser cross-linking can induce corneal haze for up to about 1 year. These results are further illustrated in FIGS. 7A-7B. FIG. 7A illustrates images of a hematoxylin and eosin stained cornea after 6 weeks of Cu treatment. FIG. 7B illustrates images of a hematoxylin and eosin stained retina/choroid after 6 weeks of Cu treatment.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A method of treating keratoconus, comprising:
administering to an eye of a subject in need thereof a therapeutically effective amount of a composition comprising an active agent selected from: copper sulfate, copper carbonate, copper acetate, copper chloride, copper gluconate, copper bromide, copper fluoride, copper nitrate, copper iodide, copper perchlorate, copper molybdate, copper thiocyanate, copper tartrate, copper tetrafluoroborates, copper selenide, copper pyrophosphate, GHK-copper, copper-histidine, copper-glycinate, and combinations thereof,
wherein the composition comprises from about 0.001 wt % to about 0.1 wt % of the active agent.

2. The method of claim 1, wherein the composition further comprises at least one of a tonicity agent, a solubilizing agent, a thickener, a polymer, a buffer, a pH adjuster, a preservative, and water.

3. The method of claim 1, wherein the composition has a tonicity of from about 270 mOsm/kg to about 350 mOsm/kg.

4. The method of claim 1, wherein the composition has a pH of from about 5.8 to about 7.8.

5. The method of claim 1, wherein the composition further comprises an additional active ingredient.

6. The method of claim 5, wherein the additional active ingredient is selected from: riboflavin, rose bengal, hydroxylysine, and combinations thereof.

7. The method of claim 1, wherein the composition is administered at from 1 to 4 time points per day per eye in need thereof.

8. The method of claim 7, wherein from about 5 μl to about 50 μl of the composition is administered at each time point.

9. The method of claim 1, wherein the composition is administered for a treatment period of at least about 1 month in duration.

10. The method of claim 1, wherein the therapeutically effective amount decreases corneal diopter as compared to the corneal diopter without treatment.

11. The method of claim 1, wherein the composition does not comprise an additional active ingredient.

12. A method of treating keratoconus, comprising:
administering to an eye of a subject in need thereof a therapeutically effective amount of an ophthalmic composition consisting essentially of an aqueous solution of a copper salt selected from: copper sulfate, copper carbonate, copper acetate, copper chloride, copper gluconate, copper bromide, copper fluoride, copper nitrate, copper iodide, copper perchlorate, copper molybdate, copper thiocyanate, copper tartrate, copper tetrafluoroborates, copper selenide, copper pyrophosphate, GHK-copper, copper-histidine, copper-glycinate, and combinations thereof, wherein the composition comprises from about 0.001 wt % to about 0.1 wt % of the copper salt.

13. The method of claim 12, wherein the copper salt is copper sulfate.

* * * * *

UNITED STATES PATENT AND TRADEMARK OFFICE
CERTIFICATE OF CORRECTION

| | | |
|---|---|---|
| PATENT NO. | : 11,065,275 B2 | Page 1 of 1 |
| APPLICATION NO. | : 16/083865 | |
| DATED | : July 20, 2021 | |
| INVENTOR(S) | : Balamurali K. Ambati et al. | |

It is certified that error appears in the above-identified patent and that said Letters Patent is hereby corrected as shown below:

In the Specification

Column 1; Line 9, Add:
--GOVERNMENT INTEREST
This invention was made with government support under grant numbers R44EY031224, R43EY027636, and R44EY031224 awarded by the National Institutes of Health. The government has certain rights in this invention.--

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*